United States Patent [19]
Takami et al.

[11] 4,288,774
[45] Sep. 8, 1981

[54] GAS DETECTOR
[75] Inventors: Akio Takami; Toshitaka Matsuura; Tsutomu Saito, all of Wagoya, Japan
[73] Assignee: NGK Spark Plug Co., Ltd., Nagoya, Japan
[21] Appl. No.: 112,977
[22] Filed: Jan. 17, 1980
[30] Foreign Application Priority Data
Jan. 18, 1979 [JP] Japan .............................. 54-5649[U]
[51] Int. Cl.³ ............................................. H01L 7/00
[52] U.S. Cl. ........................................ 338/34; 422/98
[58] Field of Search ............ 338/34, 28, 22 R, 225 D; 73/27; 23/232 E; 422/98, 83

[56] References Cited
U.S. PATENT DOCUMENTS 4,001,758 1/1977 Esper et al. ........................... 338/34
4,013,592 3/1977 Matsuoka et al. ............. 338/22 R X
4,130,797 12/1978 Hattori et al. ................... 73/27 R X
4,147,513 4/1979 Bienkowski et al. ............. 23/232 E
4,206,173 6/1980 Yamaguchi et al. ................ 422/198

Primary Examiner—C. L. Albritton
Attorney, Agent, or Firm—Sughrue, Rothwell, Mion, Zinn and Macpeak

[57] ABSTRACT

A gas detector including a gas sensitive element that provides an electrical resistance which varies with the type of gas detected and lead wires for conducting the electrical signal from the gas sensitive element. A porcelain tube supports the gas sensitive element the lower part of which is positioned within a slot in the tube. Through holes in the tube receive the lead wires. A housing encloses the tube. Only the upper part of said gas sensitive element which is not positioned within the tube is provided with electrodes.

4 Claims, 5 Drawing Figures

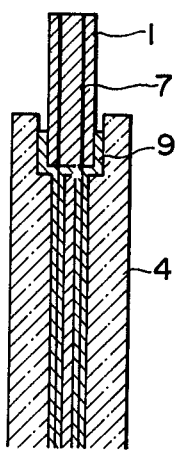
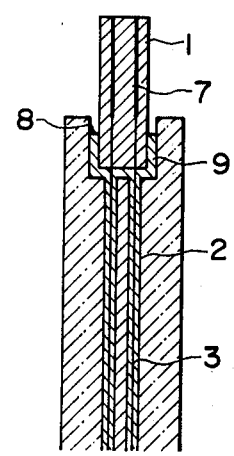
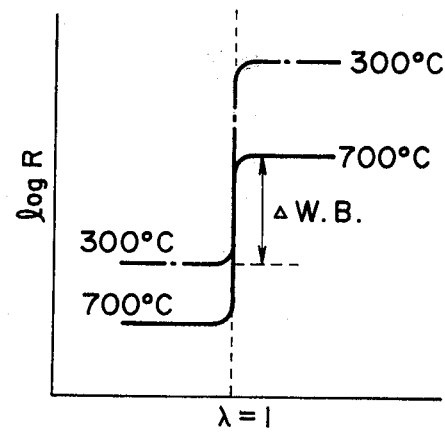
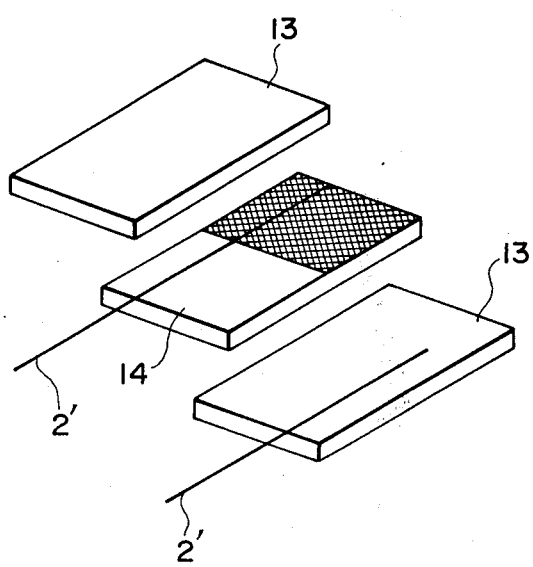
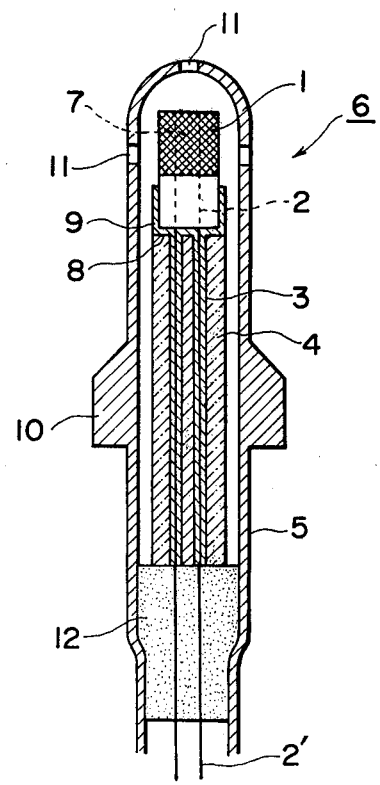

GAS DETECTOR

BACKGROUND OF THE INVENTION

1. Field of the Invention

The invention relates to a gas detector provided with a porous gas sensitive element.

2. Description of the Prior Art

The electrical resistivity of a sintered body of metal oxide semiconductors such as titanium dioxide varies with the type of gas it contacts therefore making such materials useful as gas sensitive elements as shown in U.S. Pat. Nos. 3,886,785 and 3,933,028. Such elements are typically supported with a refractory adhesive in a slot in the upper end of the ceramic insulator tube so as to provide a gas detector. However, a conventional gas detector, which is generally shown at 1 in FIG. 1 is provided with electrodes 7 that extend from the top to the bottom of the element 1 and which extend halfway down into a porcelain tube 4. Therefore, a refractory adhesive 9 impregnates into the porous lower half of the element 1, and gas sensitivity of sensor element is diminished, and the response time of the element is undesirably increased.

A gas sensitive element for use in a detector for the air/fuel ratio of vehicle exhaust gas must be such that it exhibits a sudden change in its electrical resistance at the theoretical mixing ratio ($\lambda = 1$). The electrical resistance of such an element also varies with temperature. To detect the theoretical mixing ratio, it must have a certain amount of overlap for sudden changes in electrical resistance (the overlap to be hereunder referred to as $\Delta W \cdot B$) at the theoretical mixing ratio within the operating temperature range of the air/fuel ratio detector. That is, it is advantageous to provide wide overlapping range relative to different temperature in order to detect the gas irrespective of its temperature. Such overlap is shown in FIG. 5. A conventional gas sensitive element however does not have a sufficient level of $\Delta W \cdot B$ to provide for accurate detection of the theoretical mixing ratio.

SUMMARY OF THE INVENTION

As a result of studies to find a gas sensitive element free from the defects mentioned above, the inventors have found that these defects can be eliminated by restricting electrodes in only the upper part of the element which is not embedded in the ceramic insulator tube.

Thus, in accordance with the present invention, there is provided a gas detector including a gas sensitive element that supplies an electrical signal that varies with the type of gas detected, lead wires for conducting the electrical signal from said gas sensitive element, a ceramic insulator tube for supporting the gas sensitive element the lower part of which is positioned within the tube and for receiving the lead wires in through-holes provided therein, and a housing for enclosing the tube with only the upper part of the gas sensitive element which is not positioned within the tube being provided with electrodes.

BRIEF DESCRIPTION OF THE DRAWINGS

FIG. 1 is a cross-sectional side view of a conventional gas sensitive element;

FIG. 2 is a cross-sectional side view of a gas sensitive element according to a preferred embodiment of the gas detector of the present invention;

FIG. 3 is an exploded view of the gas sensitive element of FIG. 2;

FIG. 4 is a cross-sectional front view of a gas detector incorporating the gas sensitive element according to the embodiment of FIG. 2; and FIG. 5 is a graphical representation showing the relationship between resistivity R and air/fuel ratio.

DETAILED DESCRIPTION OF THE INVENTION

The invention will now be described by reference to a preferred embodiment illustrated in the accompanying drawings wherein a gas sensitive element, hereafter referred to simply as an element, is generally indicated at 1. The element has a rectangular cross section and is made of sintered $TiO_2$, $CoO$ and $SnO_2$, $Nb_2O_3$, $Cr_2O_3$, $CeO_2$, $LaCrO_3$ or another metal oxide that exhibits different electrical resistivities depending upon the type of gas detected. A pair of electrodes 7 are positioned in the upper approximately half area of the element and are connected to a pair of lead wires 2. The electrodes 7 provide an external connection for the electrical resistances exhibited by the element 1. The ceramic insulator tube 4 is made of a heat resistant and electrically insulating metal oxide such as alumina and mullite. A slot 8 for receiving the element is provided in the top of the tube 4. The tube 4 is also provided with through-holes 3 for receiving the pair of lead wires. The element 1 is positioned and attached halfway down in the slot 8 with an inorganic adhesive such as water glass or alumina cement. The pair of lead wires 2 connected to the electrodes 7 are inserted into the through-holes 3. Indicated by 5 in FIG. 4 is a housing made of a heat resistant metal and having a flange 10. The upper part of the housing that covers the element 1 is provided with a plurality of air vents. The housing is attached to the tube 4 by means of a gas-impermeable filler 12 such as glass or alumina cement.

An exemplary method of preparing the gas detector 6 illustrated in FIG. 4 is described below. A $TiO_2$ powder is mixed with a butyl resin and ethyl alcohol to make a slurry which is formed with a doctor blade into three sheets with a thickness of 0.1 to 1.0 mm after drying. Two of the sheets are outer-layer forming sheets 13 while the remaining is an intermediate-layer forming sheets 14. The sheets are then dried to vaporize the alcohol and are cut into a predetermined size. A paste of noble metal 9 separately prepared by mixing the powder of a noble metal such as Pt or Pt-Rh with an organic solvent such as butylcarbitol acetate and an organic binder such as ethyl cellulose is screened on both sides of the intermediate-layer forming sheets 14 to cover substantially the upper part of the sheet and this metallization act as an electrode of the sensor. With a lead wire 2 made of a noble metal placed on either side, the sheet is laminated between the two outer-layer forming sheets 13 to form a three-layered element. The element is then heated to a temperature of between 150° and 700° C. to remove the organic binder by burning and is subsequently fired at 900° to 1500° C. to form the element 1. A wire of a heat resistant metal such as nickel is welded to each of the lead wires 2 to form extension leads 2, which are slide into the through-holes 3 of the ceramic insulator tube 4. The element 1 is positioned about halfway down in the slot 8 and the space between the ceramic insulator tube 4 and the element 1 is filled with a refractory cement 9. The ceramic insulator tube 4 is then placed into a metal housing 5 and attached to the housing by means of a gas-impermeable filler 12. The entire assembly is heated to a temperature of between 500° and 1200° C. to increase the strength of the cement 9 and to make the filler 12 entirely gas-impermeable.

The inventors have compared the response time of a gas detector constructed in accordance with the present invention with that of a conventional type of gas detector as illustrated in FIG. 1 and which was prepared by the same method as described above except that the metallization of noble metal was provided over the entire surface of the intermediate-layer forming sheet. A digital resistance meter was used to measure the response time. The results of the comparison are shown in the following table from which it may be seen that the gas sensitive element which was attached to the ceramic insulator tube of the detector suffered little degradation in its inherent response characteristics.

TABLE

|  | Element alone*1 | | Gas detector*2 | |
| --- | --- | --- | --- | --- |
|  | Response time at 300° C. | Response time at 700° C. | Response time at 300° C. | Response time at 700° C. |
| Conventional | 2.20 (sec.) | 4.95 | 3.10 | 6.92 |
| The invention | 2.20 | 4.95 | 2.30 | 4.98 |

*1The element was not attached to the ceramic insulator tube.
*2The element was attached to the ceramic insulator tube with an adhesive and placed in a housing to form a gas detector assembly.

For the element alone, the response time at 700° C. or 300° C. was measured in the following manner. A gas detector element was placed in a furnace held at 700° C. or 300° C. The element had a resistance of 32 ohms at 700° C. when a fuel rich gas comprising 2000 cc/min of $N_2$ containing 1 vol. % of $H_2$ was passed through the furnace and a resistivity of 8 k$\Omega$ when a lean fuel gas comprising a mixture of 2000 cc/min of $N_2$ containing 1 vol. % of $H_2$ and 100 cc/min of air was passed through the furnace. When a solenoid valve switched from lean gas to rich gas, a sharp drop occurred in the resistance of the detector element. The time ($t_1$) for the resistance to reach 8 k$\Omega$ upon switching from rich gas to lean gas divided by two was assumed to be the response time.

As is apparent from the foregoing description, a gas detector of the invention eliminates electrodes in the area of the element embedded in the ceramic insulator tube and accordingly provides a quick response time with increased $\Delta$W·B. The probable reason for this effect is that a fresh gas permeates the unembedded part of the element replacing the old gas and that the unembedded part primarily serves as a gas sensitive element instead of the embedded part which is substantially ineffective as part of the element because of lack of metallization. In contrast, the conventional gas detector has full electrodes that extend into the embedded areas of the element and fresh gas cannot easily permeate through such an area. No matter how easily the gas may permeate through the unbedded area, this is offset by minimum permeation through the other areas thus impairing the overall performance of the element.

What is claimed is:

1. A gas detector comprising: a gas sensitive element having an electrical resistance which varies with the type of gas with which said element is in contact, at least first and second electrodes coupled to said gas sensitive element, lead wires operatively coupled to said electrodes of said gas sensitive element, a ceramic insulator tube for supporting said gas sensitive element, said gas sensitive element having a lower part and an upper part, the lower part of said gas sensitive element being positioned in a slot in said tube and said tube having through holes provided therein for receiving said lead wires and a housing for enclosing said tube, said electrodes being provided only in the upper part of said gas sensitive element which is not positioned within said insulator tube.

2. The gas detector of claim 1 wherein said gas sensitive element comprises first, second and third sheets of a metal oxide of which the resistivity varies with the type of gas with which said element is in contact, layers of noble metallization disposed over at least portions of both sides of said second sheet, noble metal wire being positioned in contact with said layers of said metallization, and said first, second and third sheets being laminated to form a three-layered element.

3. The gas detector of claim 2 wherein said electrodes are made of a noble metal.

4. The gas detector of any of claims 1 to 3 wherein said gas sensitive element comprises a material selected from the group consisting of: $TiO_2$, $CoO_1$, $SnO_2$, $Nb_2O_3$, $Cr_2O_3$, $CeO_2$ and $LaCrO_3$.

* * * * *